United States Patent [19]

Hughson

[11] Patent Number: 4,918,993
[45] Date of Patent: Apr. 24, 1990

[54] METHOD OF GAUGING PRE-EXISTING IN-SITU STRESS FROM AN EXTRACTED SAMPLE

[76] Inventor: David R. Hughson, 217 Rosedale Heights Drive, Toronto, Ontario, Canada, M4T 1C7

[21] Appl. No.: 88,154

[22] Filed: Aug. 21, 1987

[30] Foreign Application Priority Data

Aug. 21, 1986 [GB] United Kingdom ................. 8620389

[51] Int. Cl.$^5$ .............................................. G01N 3/06
[52] U.S. Cl. ......................................... 73/801; 73/587
[58] Field of Search ........................... 73/153, 801, 587

[56] References Cited

U.S. PATENT DOCUMENTS

| | | | |
|---|---|---|---|
| 3,774,443 | 11/1973 | Green et al. | 73/801 |
| 3,811,734 | 10/1975 | Mehdizadeh | 73/801 |
| 4,089,224 | 5/1978 | Scott et al. | 73/801 X |
| 4,107,981 | 8/1978 | Kanagawa et al. | 73/801 |
| 4,232,558 | 11/1980 | Jon et al. | 73/801 |
| 4,344,326 | 8/1982 | Kahn | 73/801 X |
| 4,468,965 | 9/1984 | Blackburn | 73/801 X |
| 4,562,736 | 1/1986 | Iwasaki et al. | 73/587 |

FOREIGN PATENT DOCUMENTS

| | | |
|---|---|---|
| 0852771 | 2/1950 | Fed. Rep. of Germany . |
| 0879373 | 11/1981 | U.S.S.R. ................................ 73/801 |
| 1348086 | 3/1974 | United Kingdom . |

OTHER PUBLICATIONS

Dunegan et al., "Acoustic Emission", Research/Development, May 1971, pp. 20-24.
Lord, Jr., et al., "Acoustic Emission Behavior ... Bearing Capacity", Materials Evaluation, May 1976, pp. 103-108.
Koerner et al., "Acoustic Emission Behavior or Granular Soils", Journal of the Geotechnical Engineering Division, vol. 102, GT7, pp. 761-773, Jul. 1976.
Frederick, "Acoustic Emission as a Technique ... Testing", Material Evaluation, Feb. 1970, pp. 43-47.
R. V. Williams' Article Entitled "Acoustic Emission", Published by Adam Hilger, Ltd., Bristol (1980), pp. 108-116.

Primary Examiner—Eugene R. Laroche
Assistant Examiner—Seung Ham
Attorney, Agent, or Firm—Banner, Birch, McKie & Beckett

[57] ABSTRACT

Method and apparatus for determining a point of inflection in a evaluating maximum prior stresses to which a sample has been subject is accomplished by acoustical emission response from the sample versus the applied stress to the sample. The method comprises applying a compressive force to the sample in a manner which gradually and uniformly increases stress on the sample. Stress as applied to the sample is measured and simultaneously, cumulatively acoustic emission pulses are counted in response to the gradually increasing applied stress to the sample. In an X-Y co-ordinate system, the measured stress is plotted along one co-ordinate and the cumulative acoustic emission count supplied along the other co-ordinate to develop a curve having a recognizable point of inflection to indicate maximum prior stresses to which the sample had been previously subjected.

1 Claim, 9 Drawing Sheets

FIG. 3a CONTINUOUS PROFILE

FIG. 3b SEMI-LOG CONTINUOUS PROFILE

FIG. 3c PARTIAL CONTINUOUS PROFILE

METHOD OF GAUGING PRE-EXISTING IN-SITU STRESS FROM AN EXTRACTED SAMPLE

FIELD OF THE INVENTION

This invention relates to a new and novel method of detecting certain characteristics of materials. These characteristics can be interpreted from the acoustic emission response of the material when subjected to uniaxial compressive force. The characteristics of the material are inferred from testing a sample from a mass of that material on the basis that the sample is a valid representation of the mass from which it was extracted.

BACKGROUND OF THE INVENTION

Specifically, the characteristics which can be thus detected or estimated by the application of this invention are:

the maximum uni-axial or deviatoric stress which had been imposed within its recollection span on the mass prior to the sample's extraction;

the maximum amount of sustained continuous stress that the material could withstand yet remain structurally stable;

the rate of change of stress in a rising stress situation;

the distribution of localized stresses within a structural member;

the characterization of different materials based on their acoustic emission response to stress.

The design of an adequate support structure requires two basic data components: the magnitude of the stress to be carried; and the strength of the selected structural material. In a structure such as a mine or major civil engineering excavation, the reliability of both of these data components may be in doubt. Furthermore, the manner, direction and speed of the structure's response to the excavation operations, which obviously reduce the size or alter the strength of the remaining structure, is also in doubt. In order to allow for these doubtful but critical factors, it is normal practice to generously dimension the remaining structure. The effect of this conservative practice may be vastly greater strength than actually needed accompanied by low extraction ratio and elevated production and construction costs. Conversely, if the stresses were to become higher than anticipated, evidence of this fact might remain unnoticed until the situation becomes acutely hazardous.

There are several conventional methods of estimating the current in-situ stress level in a rock mass. The principal method, called over-coring, involves the cementing-in of strain gauges at the location of test and with them, detect the amount of expansion in the rock as it becomes isolated from its surrounding environmental stress by the passage of a much larger diameter core drill which surrounds the immediate region of the test location. This process is characterized by high cost and prolonged time requirement thus making extensive or multiple testing impracticable.

The substance of this invention is a new and novel method of determining, among other things, the maximum in-situ stress that had existed in a rock mass prior to the extraction of a testing sample from it.

A phenomenon of nature is that when many substantially inelastic materials such as, but not limited to, rock, concrete, ceramics, glass, rigid plastics and metals are subjected to compressive stress, they emit ultrasonic pulses known as acoustic emissions (AE). One of the behavioral characteristics of AE is that when the stress on a sample is relaxed from a level of previous maximum and then restressed, there is a significant increase in the rate of AE output as the restressing exceeds the previous maximum level. This charateristic increase of AE at the transition from past experience stress into the new experience range has become known as the Kaiser Effect. This phenomena was originally disclosed in West German patent No. 852,771 issued Oct. 20, 1952 to J. Kaiser. Other patents involving the use of the Kaiser Effect in material stress determinations are U.S. Pat. Nos. 3,774,443 and 4,107,981.

It is a further noted natural characteristic of AE that a sample of material extracted from its native environment, carries in it a Kaiser Effect recollection of the maximum stress to which that environment has been subjected.

It is an object of this invention to provide a process by which the Kaiser Effect recollection in a sample may be recalled, and a specific practical means for accomplishing this.

Another behavioral characteristic of AE, discovered in conjunction and associated with this invention is that if the stress is raised to a new experience level and held there, the AE output continues, but at a substantially exponentially decaying rate. This rate of decay is inversely related to the level of stress as a proportion of the sample's strength. As the level of constant stress approaches the strength limit of the material, the rate of exponential decay becomes slower. At some stress level, the AE will continue unabated and then start increasing. Unless the stress is released, the AE output will accelerate until gross failure occurs. Up to some stress level, the AE output will diminish to substantially zero, but higher than this level it would be likely to start accelerating within a practical future time period, the material is said to be at its Stability Limit Stress.

It is another object of this invention to provide a process by which the level of Stability Limit Stress may be estimated for a particular material, and utilizing the specific facilities provided to determine the Kaiser Effect recollection in a sample of its previously stressed environment.

This invention utilizes two parameters, namely; stress imposed on a specimen, and the AE output from it resulting from that stress. These two parameters, according to this invention, are interrelated. The relationship between them can, therefore, be graphically represented by a series of points, each representing by its position, a combination of the component amounts of AE and stress. These points could be sufficiently close together to merge into a plot line. In this invention, inferences are drawn from the resulting plot of these two simultaneous parameters.

It is recognized that, although a broad variety of materials produce AE when stressed, the plotted relationship of AE versus stress will differ between types of materials. There is also some difference between the plots of the same type of material if the stress is applied in a different direction relative to that material's natural bedding plane or some such directional characteristic. These distinctive differences in the plots of different materials may be manifested in such factors as, but not limited to, the degree of slope, curvature, direction, or abruptness of change in one or more regions of the plot, and the amount of AE total and stress at failure, and the pattern produced during the failure process.

If it were established that AE bears a relationship to strain of the material under stress, the pattern of the relationship between AE and stress could provide valuable insight into the manner in which different types of materials respond to stress.

It is a further object of this present invention to provide a process by which materials can be characterized by their individual patterns of AE responses relative to the stress causing them, giving facility to comparing AE Signature Profiles of different materials. This process will utilize the specific facilities provided to determine the Kaiser Effect recollection in a sample of its previously stressed environment.

It is recognized that the several processes for the preparation of semi-finished specimens may be accomplished through the utilization of commercially available machine tools, in some cases requiring special modifications and adaptations. However, unless such tools are already available for the use of those wishing to prepare such specimens, the obtaining of such commercial machine tools and making the necessary adaptations to them, would involve unjustifiably high capital cost, excessive use of space, the requirement of particular operator skills, would only utilize a small proportion of the capabilities to the equipment, and would be a cost-inefficient method of producing the semi-finished specimens.

It is a further object of this present invention to provide a specialized machine, combining in a single unit, or a plurality of units, the necessary facilities to economically and efficiently produce semi-finished specimens from the provided sample material.

SUMMARY OF THE INVENTION

According to an aspect of the invention, a method of identifying a point of inflection towards determining maximum prior stresses to which a specimen has been subjected by acoustic emission response from the specimen versus applied stress to the specimen when the sample is subjected to testing compressive forces comprises applying a compressive force to the specimen in a manner which gradually and substantially uniformly increases stress on the specimen, measuring stress applied to the specimen and simultaneously cumulatively counting acoustic emission pulses from the specimen in response to the gradually increasing applied stress, plotting in an X-Y co-ordinate system the measured stress and the cumulative acoustical emission counts to develop a curve having a recognizable point of inflection related to maximum prior stress to which the specimen had been previously subjected.

In accordance with another aspect of the invention, a sample is extracted from its native location in a manner to avoid imparting any additional undue stress on the sample, by drilling the ground location with a core drill to remove a cylindrical rod of material, optionally subcoring the cylindrical specimen to a diameter for testing, cutting the cylindrical sample of testing diameter to produce a specimen blank, treating both ends of the blank to produce smooth precisely parallel ends which are perpendicular to the cylindrical axis of the cylindrical blank, applying to each the treated end of the blank a curable epoxy composition, covering each end having fresh epoxy composition applied thereto with a non-bonding sheet of material, applying pressure to both sheets at the ends of the blank to extrude the applied epoxy composition from under the sheets and allow the epoxy composition to cure and harden to provide solid end caps on the specimen blank.

According to another aspect of the invention, apparatus is provided for testing a prepared specimen comprising opposing loading faces having specimen end cap contacting faces hard, flat and ground smooth and one of which faces is precisely perpendicular to a compressive axis of the apparatus and the other face being optionally free to rotationally adapt to the plane of the specimen end cap, means for applying gradually and substantially uniformly increasing compressive force on such specimen by moving in a relative manner the loading faces towards one another, means for measuring compressive force applied by the loading faces to the specimen and a single acoustic emission detecting device for mounting directly on a portion of a cylindrical face of the specimen intermediate its ends, the detecting device having an acoustic emission transducer for converting pulses emitted by such specimen under stress into detectable electronic signals, means for holding the detecting device in contact with such specimen, means for electronically filtering the electronic signals to pass only those signals in a frequency range typical of acoustic emission signals, means for cumulatively counting number of signals passed by the filter means.

According to a further aspect of the invention, apparatus is provided for preparing a cylindrical specimen for testing to determine maximum prior stresses to which such specimen was previously subjected, the apparatus comprising a rotary grinding face perpendicular to an axis of rotation for the grinding face, means for rotating the grinding face about the axis, means for securely holding a cylindrical specimen to present an end portion adjacent the grinding face, the holding means having a central longitudinal axis coincident with an axis of a cylindrical specimen, the holding means axis is offset from the axis of rotation, the holding means being supported by means which permits movement of the holding mean axially along the holding means axis and rotation of the holding means about the holding means axis to permit thereby movement of a specimen end into contact with the grinding face and rotate a specimen end relative to the grinding face, the offset of the holding means axis relative to the axis of rotation being such to maintain the sample end within the perimeter of the rotating grinding face where the grinding face annulus width is larger than a cylindrical specimen end.

Other objects and features of the present invention will become apparent from the detailed description of the preferred embodiment thereof, which will be read with reference to the accompanying drawings.

BRIEF DESCRIPTION OF THE DRAWINGS

Preferred embodiments of the invention are shown in the drawings, wherein.

DETAILED DESCRIPTION OF THE PREFERRED EMBODIMENTS

The purpose of this invention is to provide a method for preparing and testing specimens to depict their acoustic emission response relative to increasing amounts of stress and to physically interpret that relationship in such a manner that a Kaiser Effect discontinuity in the relationship continuum could be recognizable. The method comprises the utilization of tack specific equipment and/or specialized procedure for the preparation of testing specimens in order to reduce the generation of extraneous noise which could be confused with AE during testing. The method further comprises the applying of gradually and substantially uniformly increasing stress to the test specimen, during which procedure the amount of stress imposed and the cumulative count of acoustic emission pulses from the specimen are recorded. The method further comprises a procedure for converting these date acquired during the testing of the specimen into a graphical form enabling the recognition of the stress level at which an increasing rate of acoustic emission relative to the increasing stress is indicative of the discontinuity characteristic of the Kaiser Effect.

A sample of material extracted from its native environment serves as the source body from which testing specimens are prepared in order to gauge the amount of stress which had been imposed on that sample by its environment. The specimen comprises a cylindrical core of the material extracted from the sample, cut to appropriate length and the ends ground essentially smooth and precisely parallel and perpendicular to the cylindrical axis. Both ends of the specimens have applied to them a thin film of epoxy material such that it covers the complete ends, with some excess being extruded beyond the edges of the end, to form an end cap at each end of the specimens. This end cap is produced by the application of a quantity of mixed, but still viscously liquid epoxy material to each end of the specimen and onto which is applied a piece of bright-surfaced thin metal foil of a size substantially greater than the specimen end which has been thinly coated with a parting agent to prevent the foil from adhering to the cured epoxy. The specimen, together with the liquid epoxy and foil pieces is then clamped axially between two clamping faces of a size substantially greater than the specimen ends and being of a high order of smoothness and hardness and with freedom to adjust the plane of surface to conform with parallelism of the specimen ends. The axial clamping force is then exerted by the clamping device onto the specimen to an order of magnitude of approximately 2 MPa. During the clamping process, a quantity of the liquid epoxy should extrude out from the specimen end surfaces and form a small bead around the edges adjacent to the cylindrical ends and the foil piece. The specimen should remain thus, undisturbed, in the clamping device until the epoxy has become substantially cured. At any time following the cure of the epoxy and prior to testing of the specimen, the foil pieces may be peeled from the specimen exposing the thin smooth flat film of epoxy forming the end caps.

An apparatus for applying a uniaxial compressive stress to the prepared specimens comprises opposing loading faces having a high order of flatness, smoothness and hardness is contacted with the specimen end caps and with freedom to adjust the plane of at least one of their faces to conform with the parallelism of the end cap surfaces of the specimen located substantially coaxially in the apparatus.

A method of preparing specimens of material for testing and a method and procedure for conducting such testing and a procedure for the assembly of the data derived from such testing to enable the identification of the relationship existing between the testing stress applied to the specimen and the resulting acoustic emissions produced by it, and from the relationship of stress to acoustic emission output enable the identification of a discontinuity in the rate of acoustic emission output relative to stress which is characteristic of the natural phenomenon of Kaiser Effect.

Detailed aspects of these principles of the invention can be gathered from the following specific discussion of the apparatus for testing the specimen and preparing the specimen with reference to the drawings.

STEP ONE

A sample of the material to be tested is extracted by any suitable method from its native environment at the desired site location. Notation is made on it indicating its orientation with respect to its native environment. This sample may take the form, for example, of a standard rock core, or any other configuration having sufficient size for the extraction of a number of specimens of the desired size and direction.

The said sample is then sub-cored to specimen diameter in at least three perpendicular directions with respect to the sample's original orientation in its native environment. Sufficient number of sub-cores should thus be extracted to produce a sufficient quantity of specimens to give some statistical validity to the final results of the testing procedure. Each sub-core should be marked to indicate its orientation with respect to the native environment from whence it came.

The sub-cores are next sawed into specimen blanks having the configuration of a right circular cylinder of a length appropriate to their diameter in order to achieve a specified range of length:diameter ratio. Any specimen blanks possessing joints, cracks, chips, faults or other irregularity inconsistent with it being an apparently valid sample, should be discarded. Suitable specimen blanks should be identity marked in accordance with their orientation to their native environment.

The said specimen blanks should then be surface ground on their ends to make both end surfaces smooth, and precisely parallel, and perpendicular to the cylindrical axis, thus producing semi-finished specimens.

Figure 1:
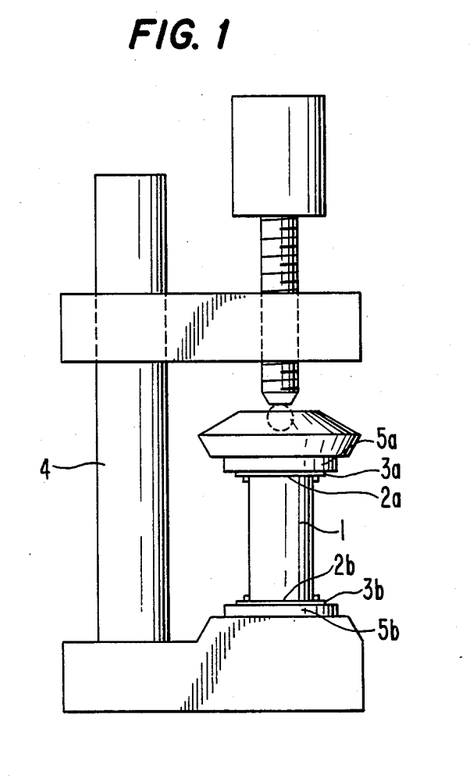
FIG. 1 is a side elevation of apparatus for applying an end-cap at each end of a specimen blank.

Each semi-finished specimen is then provided with an end-cap at each end in the following manner and as shown in FIG. 1. The semi-finished specimen 1 has a thin layer of freshly mixed epoxy or some such suitable material 2a and 2b applied uniformly over both ground end surfaces. Two pieces 3a and 3b of bright smooth metal foil or similar suitable material, of a size substantially greater than the size of the specimen end, and treated as necessary on their specimen-contact surfaces to prevent bonding with the said epoxy material, having been previously prepared and placed specimen-contact surface upward on a hard flat smooth surface. End 2a of semi-finished specimen 1 is then pressed onto the end foil 3a with a force sufficient to extrude much of the viscous epoxy to the perimeter of the end surface. Semi-finished specimen 1, now carrying end foil 3a held in position by epoxy 2a, is then reversed and end 2b is pressed in similar manner onto end foil 3b. The semi-finished specimen 1, now carrying end foils 3a and 3b, is then transported to a clamping device 4 into which it is placed approximately coaxially with the clamping force. The clamping device 4 is equipped with clamping faces 5a and 5b being hard, flat, and polished smooth and of a size substantially greater than that of the specimen end. Clamping faces 5a and 5b might be of a material such as, for example, polished glass. One clamping face 5a should be provided with a degree of rotational freedom enabling it to bear flat upon the specimen end 3a independent of any deflections within the clamping device 4. Clamping pressure is then applied to the semi-finished specimen in the approximate order of magnitude of 1 or 2 MPa further extruding epoxy interposed between specimen ends and the end foil pieces, to the perimeter of the specimen ends. Clamping pressure should be maintained for sufficient time to permit the epoxy to cure. Thus is produced a specimen, including epoxy end-caps to which are adhered, but not bonded, end foil pieces.

Figure 2:
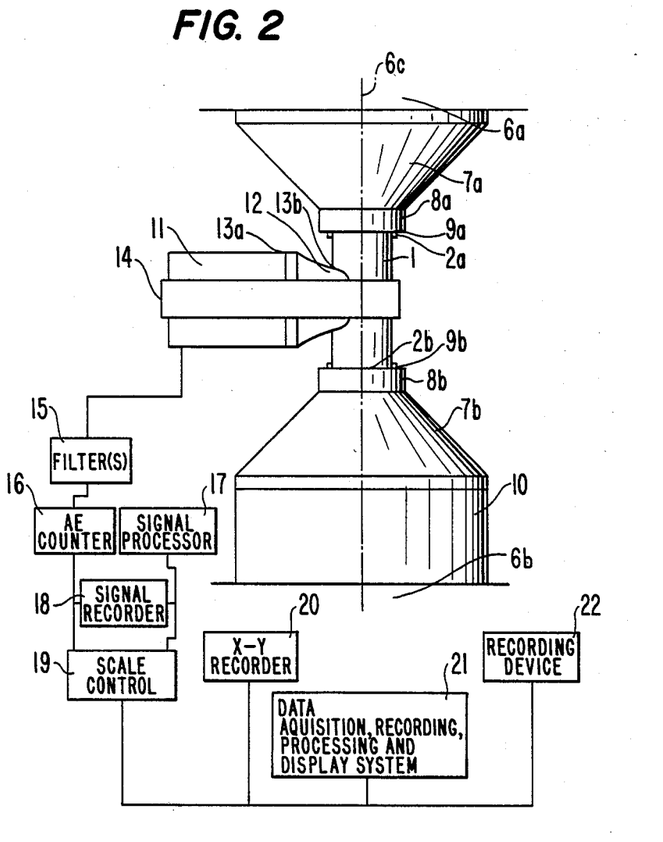
FIG. 2 is a side elevation of apparatus for testing the specimen and schematic illustration of related electronic components.

FIG. 2 schematically depicts a preferred embodiment of the specimen testing facilities. This comprises three facets, being: uniaxial compressive force application device 6a, 6b, 7a, 7b, 8a, 8b, 10; acoustic emission detecting device 11, 12, 13a, 13b, 14; and data acquisition, processing and recording equipment 15, 16, 17, 18, 19, 20, 21, 22.

The platens 6a and 6b of the compressive force application device have detachably mounted to them loading plate assemblies 7a and 7b which include fixedly mounted, very hard metallic loading faces 8a and 8b being disks of a diameter greater than that of the specimen and with specimen-contacting face being ground smooth and precisely perpendicular to the compressive axis 6c.

Interposed in the force application system is a force transducer 10 which produces an electronically detectable signal proportional to the magnitude of the axial force applied between loading faces 8a and 8b. The nature and position of the said force transducer 10 may take one of several possible embodiments depending upon the configuration and operating mechanism of the said compressive loading machine without restricting or detracting from the principle of the invention. For example, possible options for the force transducer 10 could be in the form of an axial load cell interposed between loading machine platen 6b and loading plate assembly 7b as depicted in FIG. 2; or as another possible example, in the form of a hydraulic pressure transducer located in a hydraulic feed line into a hydraulic ram actuating one of the platens 6a or 6b.

Another component of the said specimen testing facility is the acoustic emission detecting device. This consists of an acoustic emission transducer 11 capable of converting the pulses emitted by the specimen into detectable electronic signals, to which is removably attached wave-guide 12 shaped to substantially conform at one end with the detecting face of the transducer 11 and at the other end with the cylindrical side of the specimen and being of a material which readily conducts the AE energy pulses from the specimen 1 to the transducer 11. The interface between transducer 11 and wave-guide 12 is filled with a thin film of viscous material 13a known to the ultrasonics trade as a couplant, and which assists in the transmission of AE energy pulses from the wave-guide 12 to the transducer 11. The transducer and wave-guide assembly is elastically held in firm contact with the specimen side by means of an elastic band 14, or other suitable device, of appropriate size and force to be the exclusive support means for the transducer and wave-guide assembly and hold it in compressive contact against the side of the specimen 1. The interface between wave-guide 12 and specimen 1 is also filled with viscous material 13b serving as an ultrasonic couplant between the two adjacent components.

The AE transducer 11 and the force transducer 10 are both electronically connected to the third facet of the specimen testing facility, namely: the data acquisition, processing, displaying, and recording equipment.

As further depicted in FIG. 2, this equipment comprises the following components. One or more frequency filters 15 which permit the passage of only those signals from the AE transducer 11 which are within a frequency range typical of the AE signals sought, and filtering out possible extraneous signals of higher or lower frequencies. AE counter 16 being an electronic device capable of making a cumulative total count of signal pulses which are passed by the filter 15 and which are of a strength exceeding an adjustable threshold level. A signal processor 17 being an electronic device to energize the force transducer 10 and receive and interpret its output signals into electronic signals which are proportional to the force exerted upon the transducer 10. The output signals from both the AE counter 16 and signal processor 17 may be simultaneously recorded in signal recorder 18 for future replay and analysis, and/or fed direct into scale control 19 being an electronic device providing for the manual adjustment of the scales for AE count and force, independently of each other. By this device, the scales of both parameters may be individually adjusted to translate the amount represented by the raw data into an amount compatible with the full scale value of a graphical plotting device, or the input signal characteristics needed by other possible data processing or recording devices.

The output of the scale control 19 is connected to one or more of several possible types of data display, processing and/or recording devices with the aid of which the data may be analyzed and interpreted. One possible embodiment of the data display and recording system, without limiting the scope of possibilities envisaged in this invention, could be in form of an X-Y recorder 20. Another possible embodiment could be a computer oriented data acquisition, recording, processing and display system 21. By such a computational system, the data may be further processed into various forms which may serve to assist in improving the accuracy of identifying the stress level at which the Kaiser Effect took place. As an example, but without limiting the scope of this invention to it, a form in which the data may be further processed is that of a semi-log plot. In this, a linear scaled force is plotted with a logarithmically scaled AE count. It is further envisaged that the output data of the scale control 19 could be recorded in a non-graphic form by means of a recording device 22 which at some later time could be replayed through a data display device such as 20 or 21 for analysis and interpretation.

These various components 15, 16, 17, 18, 19, 20, 21, 22 of the data acquisition, processing and recording equipment may be physically and/or electronically combined in any form of collective configuration or configurations, without detracting from or reducing the principle or intent of this invention.

STEP TWO

A sample prepared in accordance with the procedure described in Step One is then subjected to a testing procedure in the afore-described specimen testing facilities, as follows. The assembly of AE transducer 11 together with wave-guide 12 is elastically mounted to the specimen 1 with couplant 13b in the interface. The end foils 3a and 3b are peeled off the specimen end-caps 2a and 2b. The exposed end-cap surfaces have applied to them a thin uniform film of high pressure lubricant 9a and 9b, such as but in no way limited to, lithium grease or molybdenum disulphide grease. The specimen and transducer assembly now consisting of items 1, 2a, 2b, 9a, 9b, 11, 12, 13a, 13b, 14 is then interposed between platen faces 8a and 8b and located approximately axially in the compression testing system 6c. The compression testing system is then actuated sufficiently that the platen faces 8a and 8b snugly grip and hold the specimen.

The data acquisition and recording system should be activated and scales adjusted to be appropriate for the type of material being tested and the type of test to be conducted on it. Compressive stress is then gradually and uniformly increased on the specimen in accordance with the type of test while both the level of stress an resulting AE response by the specimen are simultaneously and continuously recorded. The preferred embodiment of this data record takes a graphical representation in the form of a continuous line plot of increasing stress in the right-hand direction on the ordinate (X axis) and of increasing total cumulative AE count in the upward direction on the abscissa (Y axis). This form of graphical representation of stress versus AE response is herein referred to as a plot.

STEP THREE

Figure 3A:
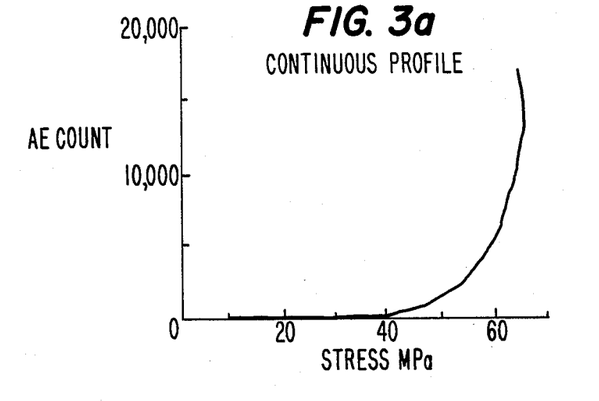
FIGS. 3a, b and c are plots of AE count versus applied stress for a particular specimen.

As a broad generality, it will be noted that materials subjected to the testing procedure as specified in this invention, emit relatively few AE signals in the low stress range but this increases as the stress rises and accelerates rapidly as the material's strength limit is approached. As the stress reaches the specimen's ultimate strength, the AE count surges upward. The shape of a plot depicting this general relationship between stress and resulting AE response would, if a single appropriate linear scale were used throughout, produce a plot somewhat as shown in FIG. 3a, displaying a characteristic low slope at low stress but the slope increasing as the stress rises and becoming very steep as the failure level is approached. If, however, the same response data were plotted using a logarithmic scale for the AE count and a linear scale for stress, the resulting plot would appear somewhat as shown in FIG. 3b.

Figure 3B:
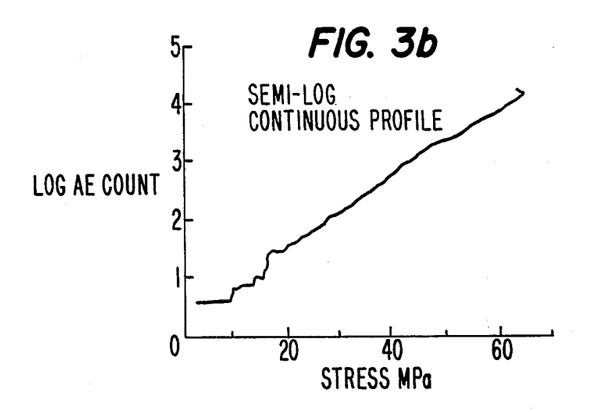

It is noteworthy, however, that specific materials produce plots which may deviate in various respects from the depicted broad generality plots shown in FIGS. 3a and 3b. Specimens of the same material and taken in the same orientation direction, tend to produce plots of a shape similar to each other. Thus it could be said that specific materials produce a characteristic plot typical of that material and might be referred to as an AE Signature Continuous Profile of that material.

Figure 3C:
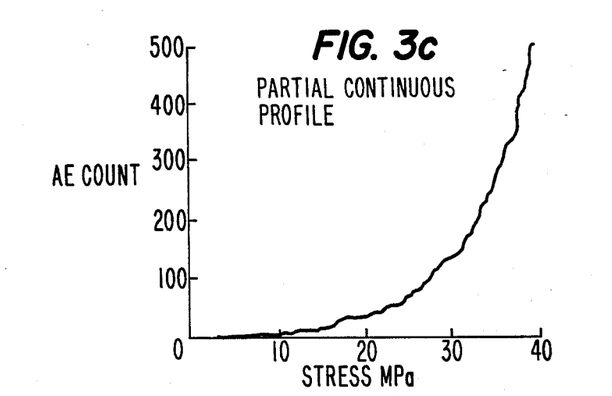

It might be apparent from the low slope in the lower stress range of the plot shown in FIG. 3a, that relatively minor changes in the rate of AE output within this range, might be difficult to identify. If however the AE count scale were expanded by a factor of, for example 40, the plot would become substantially steeper. In such an instance, relatively minor changes in the relationship between stress and resulting AE count rate would become more graphically enhanced. FIG. 3c indicates the low stress range plot of the data represented in FIG. 3a but with the AE count scale expanded by a factor of 40 times that used in FIG. 3a.

As already noted, the natural phenomenon of Kaiser Effect is manifested by a change in the rate of AE output as the increasing stress on a sample passes from the level of past experience into the range of new experience.

Figure 4A:
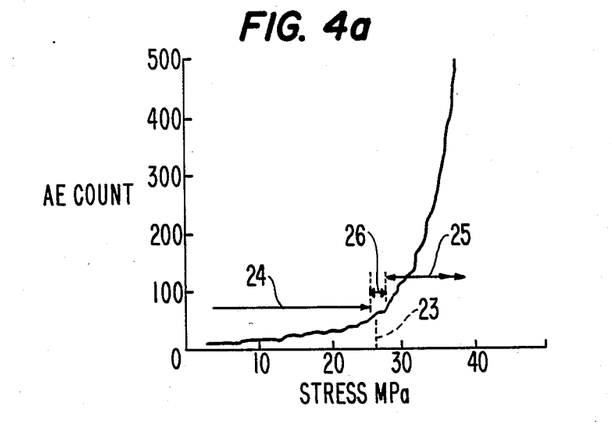
FIGS. 4a and b are plots of AE count versus applied stress for a different specimen than shown in FIG. 3.
Figure 4B:
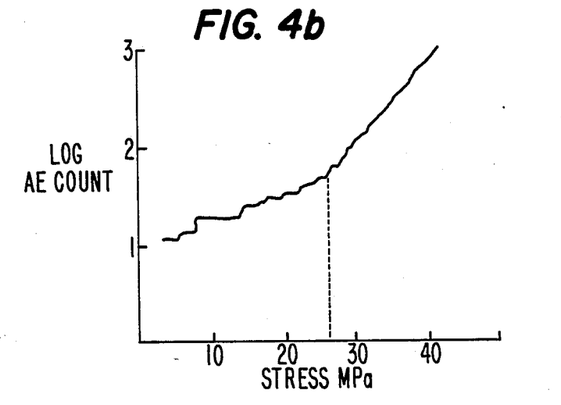

If a specimen as described in Step One had been extracted from a stressed native environment and subjected to the testing procedure described in Step Two, the degree by which the Kaiser Effect change in AE rate would become readily apparent, could be a function of the AE scale employed in producing the plot. If the scale were compressed to the extent that the complete AE Signature Continuous Profile would appear as in FIG. 3a, it is unlikely that a Kaiser Effect change could be observed. If, on the other hand, a more expanded scale such as employed in plotting FIG. 3c were used, a discontinuity of the plot would become more evident at the stress level consistent with the pre-existing maximum stress on the specimen's native environment. FIG. 4a shows the plot of the same type of material and AE scale as generated by the plot shown in FIG. 3c, but which had a pre-existing stress in the specimen's native environment of a magnitude indicated at 23 in FIG. 4a. It can be observed that the past experience portion 24 of the plot has a substantially uniform slope which is lower than the slope in the same region of FIG. 3c. It is also noted that the plot in the new experience region 25 is comparable in the same stress range for both FIG. 3c and FIG. 4a. It is also noted that the transition of plot from past experience 24 to new experience 25 takes place in a transition zone 26 and not necessarily at a clearly definable precise point. The nature, breadth and position of the transition zone 26 is subject to many variable factors such as, but not limited to, the type of material, the magnitude of stress relative to the material's strength, the duration of the environmental stress. FIG. 4b depicts the same data as was used in FIG. 4a but the AE count is presented on a logarithmic scale instead of the linear scale used in FIG. 4a. It is appreciated that the results as shown in plots of FIGS. 3 and 4 may be analyzed by computational processes to improve the accuracy in identifying the stress level at which Kaiser Effect took place.

STEP FOUR

As already noted, another behavioral characteristic of AE is that, if stress is held at a new experience level, the AE output decays at a substantially exponential rate, the rapidity of which is inversely related to the level of stress as a proportion of the sample's strength.

Figure 5:
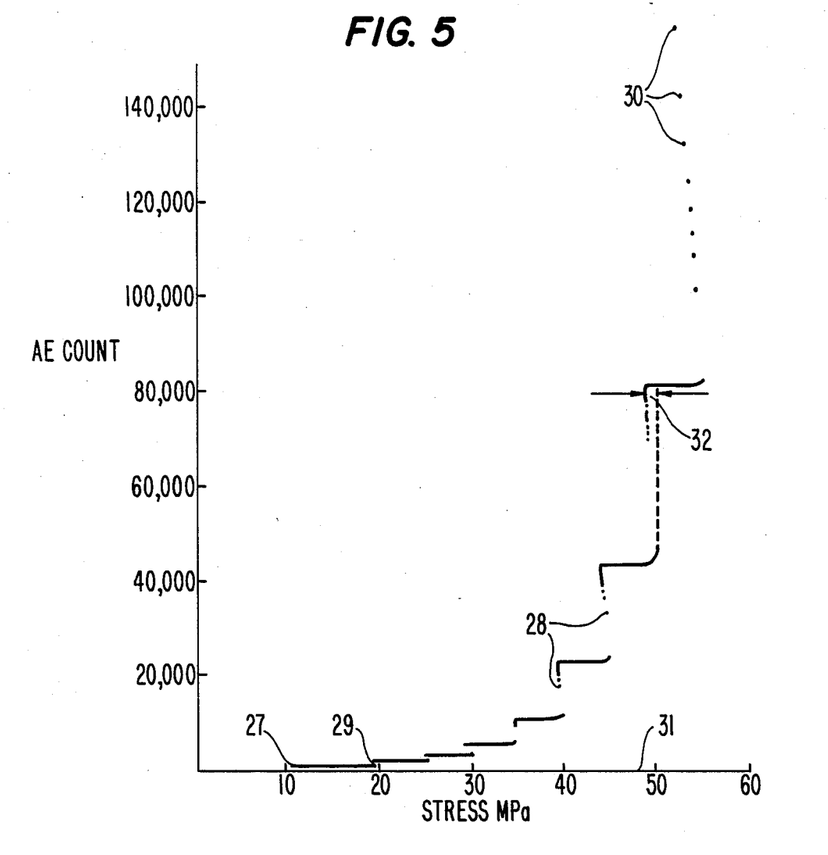
FIG. 5 is a plot depicting AE count decay when specimen stressed beyond its previously experienced higher level.

FIG. 5 is a sample plot depicting this characteristic. It is produced by a specimen prepared in accordance with Step One and subjected to stress in accordance with Step Two. In this test procedure, however, the stress is rapidly raised to an incremental level 27 at which point the application of further stress is stopped and the plotting pen is lifted from the graph page. At the end of each uniform time-lapse interval thereafter, the pen is momentarily re-engaged to produce a dot 28 on the graph page. During the first dwell time interval, it might be noted that some continuing AE output is detected, as evidenced by the raised position of the dot. During subsequent dwell time intervals, progressively fewer additional AE counts are detected, as evidenced by the subsequent dots being closer together than previous ones. When, after several dwell time intervals during which subsequent dots are substantially coincident, indicating insignificant additional AE output, the plotting pen is re-engaged to the graph page and the stress is rapidly raised to the next incremental level 29, where again the application of further stress is stopped and the plotting pen is lifted from the graph page. Once more dots are placed at the end of the same uniform time-lapse intervals until subsequent dots are substantially coincident, indicating that additional AE output had decayed to approach zero. This cycle of incremental stress increase and dwell period for AE output to decay towards zero, is repeated until subsequent dots no longer get closer together but clearly have started to diverge 30. The resulting plot which could be referred to as an AE Dwell Profile, indicates that as the stress level approaches the strength of the material, a longer time interval is required for the AE output to decay towards zero. It can be further recognized that at some stress level, the AE output could not be expected to decay towards zero, in which case it could be reasonably expected to start accelerating and proceed thus until gross failure occurs unless the stress is released. The approximate maximum stress at which the AE output appears likely to decay towards zero, is referred to as the Stability Limit Stress 31.

It might be noted also that there is an apparent loss of stress 32 that occurs during the dwell periods.

It is observable that different types of materials subjected to the AE Dwell Profile testing procedure as described under Step Four produce plots which may deviate in various respects from that depicted in FIG. 5. Furthermore, specimens of the same material and the same orientation, tend to have plots of a shape similar to each other. Thus is could be said that specific materials produce a characteristic Dwell Profile plot typical of that material. This might be referred to as an AE Signature Dwell Profile of that material.

A MACHINE SPECIFICALLY FOR THE PREPARATION OF SEMI-FINISHED SPECIMENS

Figure 6:
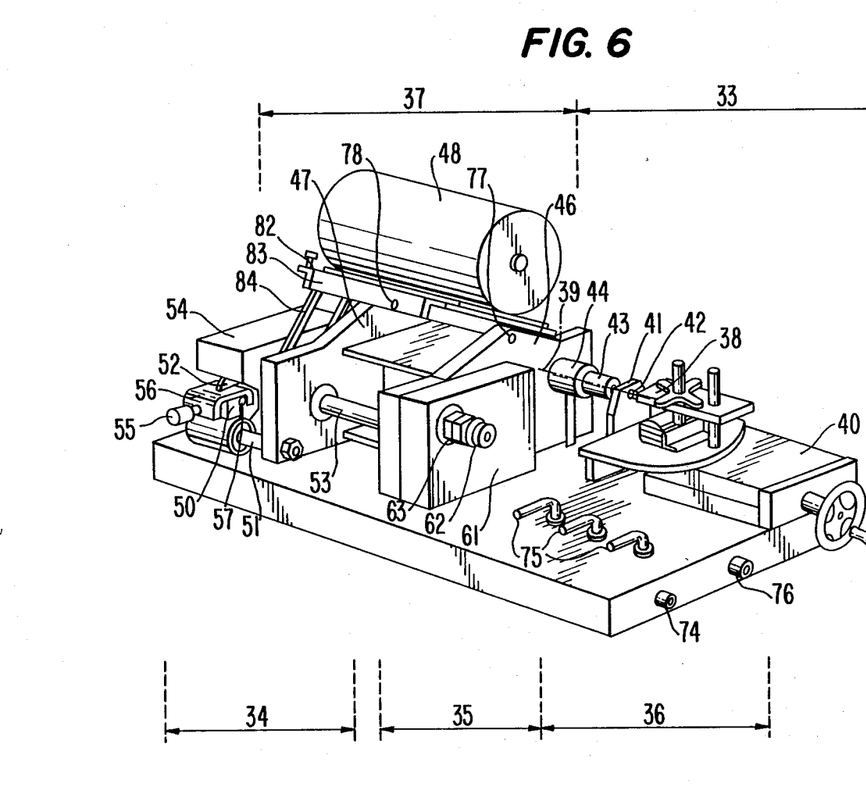
FIG. 6 is a perspective view of apparatus for extracting and preparing semi-finished specimen cores.

FIG. 6 diagrammatically represents a preferred embodiment of the Semi-Finished Specimen Preparation Machine. This comprises three distinct facets, being: drilling assembly for the sub-coring of the sample in any direction, 33; sawing assembly for end-trimming and cutting to length of the drilled sub-cores to produce specimen blanks, 34; surface grinding assembly to accurately prepare both ends of the specimen blanks to produce semi-finished specimens, 35. It also includes a system 36, for the distribution of flushing and cooling fluid to the various necessary locations and the confinement and collection of such used fluids to the extent practicable. It also includes a drive system, 37, to deliver appropriate torque and speed to the various machine facets.

DRILLING ASSEMBLY

The drilling assembly 33 consists of a sample clamping device 38 which holds the sample in a selected orientation with respect to the core-drill axis 39. This said selected clamping orientation may be in any combination of: angle of rotation about a horizontal axis; angle of rotation about a vertical axis; elevation of the specimen relative to the horizontal plane of the drill axis 39. It can also adapt to a diversity of shapes and dimensions of a sample within the construction limitations of the drilling assembly 33. The clamping device 38, is pivotally mounted by a vertical axis to a platform 40, which is feed-screw actuated and hand-wheel driven in a direction parallel to the core-drill axis 39, through a distance approximately equal to the maximum core drilling length. A drill guide 41, fixedly mounted to platform 40 and containing a through hole of diameter slightly greater than the outside diameter of the core-drill barrel 42 and being co-axial with it, provides radial restraint to the core-drill barrel 42 as the drill entry is commenced into the sample. The core-drill barrel 42 is of a length such that when platform 40 is fully retracted, the cutting portion at the end of the core-drill barrel protrudes beyond the face of the drill guide 41 in the direction of the clamping device 38; and conversely, when the platform 40 is fully advanced, the drill guide 41 still surrounds the core drill-barrel proximal to its end remote from the cutting portion and does not interfere with any barrel enlargement or mounting hub 43 of the core drill barrel 42.

The core-drill hub 43 is removably attached to a water-swivel 44 being co-axial with the drill barrel 42 and hub 43 and providing facility for the entry of cooling and flushing fluid into the central region of the core barrel 42 from a source exterior to the said barrel notwithstanding the rotation of the core-drill about its axis 39.

The water-swivel 44 is removably attached to and co-axial with the drill drive shaft 45 and core-drill axis 39. The drill drive shaft 45 is provided with rotational freedom but radial and axial restraint by means of anti-friction bearings mounted in frame plates 46 and 47. Onto the end of the drill drive shaft 45 being remote from the core-drill, and protruding beyond frame plate 47, a V belt pulley 80 is mounted having a diameter appropriately sized relative to a V belt pulley 81 on the motor 48 to convert the motor speed to the desired rotational speed of the core-drill.

SAWING ASSEMBLY

Figure 6A:
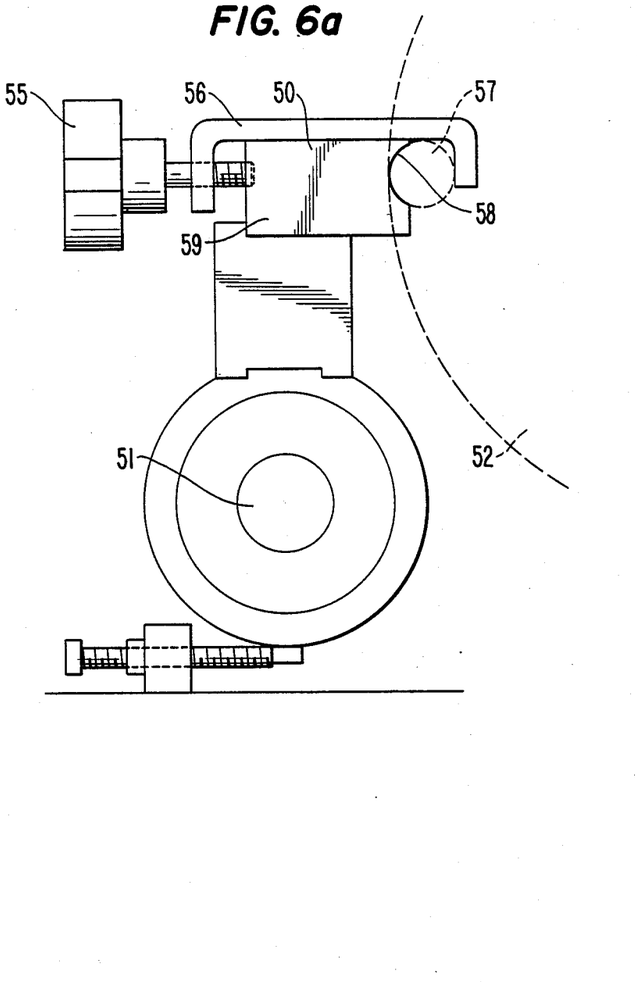
FIG. 6a is a side elevation of the sawing assembly of FIG. 6.

The sawing assembly 34, and as partially detailed in FIG. 6a, consists of a core fixture 50 with a radius of rotation about a fixed cantilever shaft 51, being removably but rigidly attached to the frame plate 47 and with its axis being parallel to the axis of the high-speed shaft 53; also a diamond cut-off wheel 52 mounted on high-speed drive shaft 53 and free to rotate within a splash confining and safety enclosure 54.

A sub-core produced by the drilling assembly 33, is held in the core fixture 50 by a thumb screw 55 actuation of a channel shaped clamp 56 which presses the sub-core 57 into a substantially semi-cylindrical recess 58 in the face of fixture block 59 which would rotate to first intersect with the cutting edge of the cut-off wheel 52, and said recess 58 having its axis of generation perpendicular to the plane of the said cut-off wheel 52. The recess 58 is of a diameter to snugly receive sub-cores as drilled by the drilling assembly 33 and being parallel to the axis of the cantilever shaft 51.

The fixture block 59 is mounted at a fixed radial distance from the axis of cantilever shaft 51 and is anti-friction bearing mounted to it, giving it rotational freedom within adjustable limits about the axis of the said shaft, but restrained from motion in axial or radial directions. The fixture block 59 is positioned by construction such that the approximate mid-axial length of the recess 58 is coincident with the plane of the cut-off wheel 52.

At the said approximate mid-axis plane of the fixture block 59, and the associated clamping channel 56, a clearance slot is provided such that when the clamping assembly on the fixture block is rotated towards the cut-off wheel 52, the said cut-off wheel will be free to enter the clamping assembly to the depth of the semi-cylindrical recess 58. A rotational stop bearing adjustably against a portion of the fixture block assembly, prevents the fixture block 59 from rotating into the cut-off wheel 52, beyond this said depth limit. Thus a sub-core 57 being located selectively and firmly clamped into the recess 58 by the action of thumb screw 55 and clamping channel 56, may be manually rotated against the cut-off wheel 52 and cut by it diametrically on a plane perpendicular to its axis and at a location governed by its selected positioning along the length of the recess 58. The selected positioning of the sub-core 57 in the recess 58 would be towards achieving the objective of trimming a sub-core end to be flat and perpendicular to its axis, and producing a specimen blank of desired length.

An enclosure 54 substantially surrounds the cut-off wheel 52 yet permits the core fixture to be rotated the required amount into maximum saw-depth position. The said enclosure serves the dual function of protecting nearby personnel from the hazards recognized in the trade as being associated with the operation of such a cut-off wheel; and also to direct and confine to the extent practicable, the cooling and flushing fluid required for the proper functioning of the cut-off wheel 52.

The high speed drive shaft 53 is provided with rotational freedom but radially and axially restrained by means of anti-friction bearings mounted in frame plates 46 and 47. Onto one end of the said shaft 53 is mounted the diamond cut-off wheel 52. Also mounted to the said shaft 53 and interposed between enclosure 54 and frame plate 47, is a V belt pulley having a diameter appropriately sized relative to a V belt pulley on motor 48 to convert the motor speed to the desired rotational speed on the said shaft 53.

SURFACE GRINDING ASSEMBLY

At the other end of the high speed drive shaft 53, being remote from the sawing assembly 34, is located the surface grinding assembly 35. This assembly consists of a tool known in the trade as a diamond cup wheel 60 mounted on the end of the high speed drive shaft 53; an enclosure 61 mounted to the frame plate 46; and a specimen blank fixture 62.

The said diamond cup wheel 60 is mounted to the said shaft 53 in such a manner to facilitate precision in the fine adjustment of the plane of the cup wheel grinding face 65 to be perpendicular to the axis of the said shaft 53.

The enclosure 61 together with the associated portion of the frame plate 46, substantially surrounds the cup wheel 60 and serves a triple function. It protects nearby personnel from the hazards recognized in the trade as being associated with such a grinding operation. It directs and confines to the extent practicable, the cooling and flushing fluid required for the proper functioning of the surface grinding operation. It further provides a rigid structure which by construction is perpendicular to the axis of high speed shaft 53, and thus by the aforesaid precision adjustment provision in the mounting of the cup wheel 60, is also parallel to the plane of the grinding surface 65. This rigid structure 61 holds the specimen blank fixture socket 63.

The specimen blank fixture socket 63 is removably fixed to the rigid structure 61 and provides a precision cylindrical through-hole of suitable diameter and of length at least twice the said diameter and with axis perpendicular to the plane of the rigid structure 61 and located in the said structure 61 such that the projection of the axis of the through-hole 64 meets with the mid-width of the grinding surface of the cup wheel 60. The specimen blank fixture socket 63 is held in position by shoulder 70 which bears on the inside surface of the enclosure face structure 61 under clamping pressure exerted by nut 71 on screw threaded portion 72 of socket 63 pressing against washer 73.

Figure 6B:
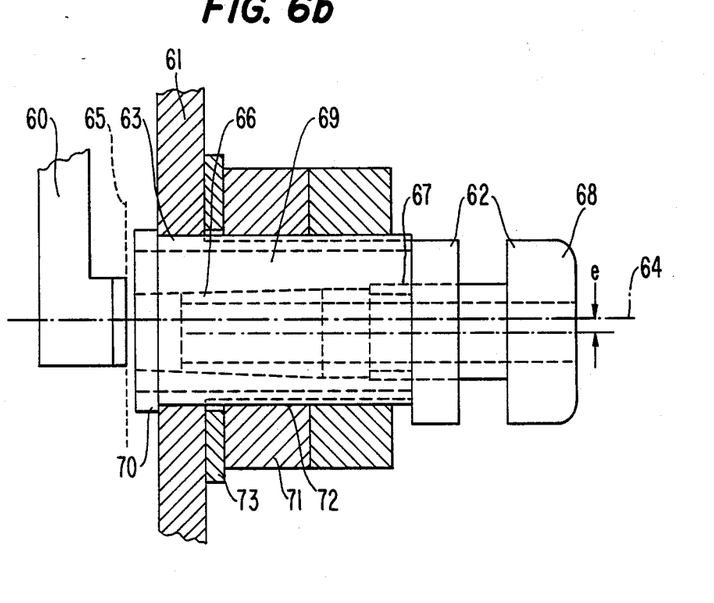
FIG. 6b is a section through the specimen Collet chuck of FIG. 6.

The specimen blank fixture 62 is diagrammatically shown in a preferred embodiment in FIG. 6b. It consists of a radial clamping device, known in the trade as a Collet Chuck, 66 with inside diameter of its through-hole being substantially equal to the exterior diameter of the specimen blanks as produced by the drilling assembly 33; and the exterior shape of which is that of a truncated cone with screw threaded uniform diameter segment 67 at its base; and an enlarged diameter shoulder segment 68, having its outer surface knurled to provide for a finger gripping surface. The Collet type chuck 66 fits into a mating chuck socket 69 with a similarly dimensioned truncated cone shape and screw threaded portion as an interior shape. The exterior shape of chuck socket 69 is that of a uniform cylinder of diameter to provide it with a sliding fit when inserted in the through-hole of socket 63. An enlarged exterior diameter shoulder is at the end of the chuck socket 69 containing the threaded portion 67, having a diameter similar to that of the knurled portion of chuck 68, and also being knurled. The axis of generation of the interior shape of socket 69 is parallel but eccentric to the axis of generation of the exterior shape 64 of the socket 69 by an amount such that substantially the whole width of the grinding face of cup wheel 60 is exposed to a specimen end as the specimen blank fixture 62 is rotated through a complete revolution without any portion of the specimen end moving beyond an edge of the grinding surface. That is; the amount of eccentricity should be as large as practicable yet such that when collet type chuck 66 is assembled into socket 69 and together are inserted into the through-hole of specimen blank fixture socket 63, the projection of the through-hole of collet type chuck 66 would fully intersect with the grinding surface of cup wheel 60 independent of the rotational position of the chuck and chuck socket assembly 62 within the fixture socket 63, and no portion of the projection of the through-hole of chuck 66 would pass beyond an edge of the said grinding surface.

When chuck 66 is mated with socket 69 and tightened together by means of screw threads 67, the mating truncated cone shapes tend to reduce the interior diameter of the through-hole in chuck 66. If a specimen blank of diameter as produced by drilling assembly 33 were to substantially occupy the through-hole in chuck 66, the tightening action of the threads 67 would cause the chuck 66 to grip the surface of the occupying specimen blank.

Thus, when a specimen blank is inserted into the through-hole of the collet type chuck 66, exposing an end protruding beyond the end of the chuck being remote from the knurled end, and which is to be ground, the specimen blank fixture 62 is tightened to grip the specimen blank by the applying of tightening torque between the two adjacent knurled segments of the mating parts 68 and 69. The specimen blank fixture 62, now carrying a specimen blank clamped by the collet action, can be inserted into the through-hole of fixture socket 63 with freedom to be moved both axially and rotationally as may be caused by manual torque and pressure exerted on the knurled surface 68 to bring the exposed specimen blank end into contact with the grinding surface of the cup wheel 60. If the high speed shaft 53 is driven by motor 48, and the cooling and flushing fluid is flowing into the enclosure 61, manually applied axial thrust on knurled portion 68 will press the specimen blank end against the grinding surface causing grinding action to occur at the said specimen blank end. Simultaneous manual torque applied to the same knurled portion 68 will cause the specimen blank end to be rotated across the grinding surface of the cup wheel 60, distributing the grinding action over substantially the whole grinding surface of the cup wheel 60, and altering the grinding action direction across the specimen blank end. This combination of axial and rotational forces on the fixture 62 and hence between specimen blank end and grinding surface, should be continued until the desired amount has been ground from the specimen blank end. If the knurled shoulder of socket 69 were to come into contact with the end of fixture socket 63, further grinding action would be prevented until the specimen blank is axially repositioned in the chuck 66 to cause its end to protrude further towards the grinding surface.

FLUSHING AND COOLING SYSTEM

Consistent with the practice of the trade, the use of diamond type drilling, sawing and grinding operations should be accompanied by a continuous flow of flushing and cooling fluid directed at a region on the diamond type surface immediately in advance of its point of contact with the workpiece. This serves to control the temperature rise caused by the cutting action, and also to flush and carry away the fines resulting from the material removal. This fluid is frequently water. If however, water might have an adverse effect on the material of the workpiece, such as, for example, being dissolved by it as in the case of salt or potash, or enter into a chemical reaction with it as in the case of some ferrous metals, some more appropriate cooling and flushing fluid might be substituted for water.

Also included as a component of the subject machine, is a system 36 for the distribution of flushing and cooling fluid to the various cutting locations, and the substantial confinement and collecting of such fluids, to the extent practicable, for disposal or recirculation.

A hose fitting 74 on the machine base is provided to connect an external supply of fluid under pressure to a plurality of valves 75, each of which when in the opened state would direct the supplied fluid, through appropriate conduit, to a specific component of the machine where a nozzle, orifice or appropriate fitting would direct the fluid to perform its function in the prescribed manner.

At the several working locations of the subject machine, provision is made to confine and collect the spent fluid to the extent practicable, and direct it by means of a waste conduit system to a discharge hose fitting 76 on the machine base. The waste fluid thus discharged should be directed to a settlement container for the removal of fines, and then may be either discharged or recirculated under pressure back into hose fitting 74.

DRIVE SYSTEM

The subject machine also includes a centralized drive system 37 to provide appropriate torque and speed to the drill drive shaft 45 and the high speed drive shaft 53. This system is further partially detailed in FIG. 6c.

Figure 6C:
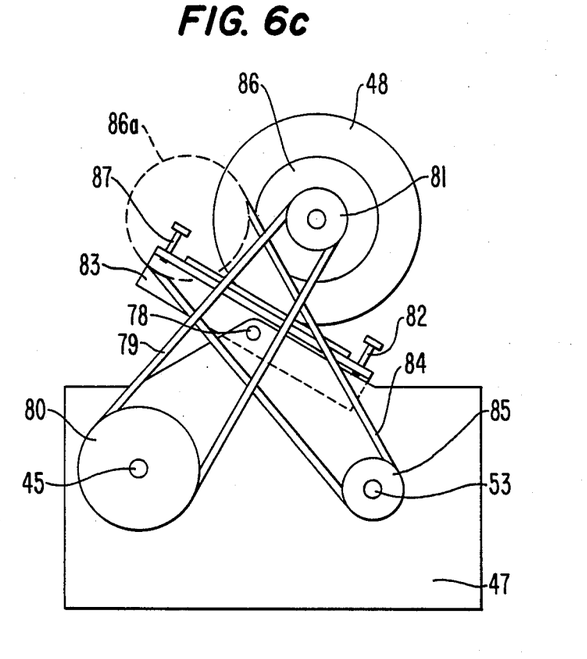
FIG. 6c is a side elevation of the centralized drive system of FIG. 6.

A motor 48, typically but not necessarily electric, of suitable power, speed and other standard characteristics, is pivotally mounted on frame plates 46 and 47 at pivot points 77 and 78 respectively. When motor 48 is tilted about its pivots in a direction away from shaft 45, as depicted in FIG. 6c, a V belt 79 of appropriate length, becomes tightened between V belt pulley 80 on drive shaft 45 and V belt pulley 81 on the shaft of motor 48. Adjustment screw 82 being screw thread mounted in motor pivot base 83 and bearing against the edge of frame plate 47, provides for a limiting adjustment to the pivot angle and hence an adjustment for the tension in V belt 79. When motor 48 is in this attitude, V belt 79 provides driving force to drill shaft 45 and at a speed related to that of the motor by the diameters of the V belt pulleys 80 and 81.

V belt pulley 86 is mounted on the motor shaft coaxially with V belt pulley 81. When motor 48 is tilted about its pivots in a direction towards drill shaft 45, V belt pulley 86 takes up a position approximately as shown in FIG. 6c at 86a. In this position, V belt 84 of appropriate length, becomes tightened between V belt pulley 85 on the high speed shaft 53, and V belt pulley 86. Similarly, an adjustment screw 87 at the opposite end of motor pivot base 83 from the position of adjustment screw 82, and bearing upon another edge of frame plate 47, provides for a limiting adjustment to the pivot angle and hence an adjustment of the tension in V belt 84. When the motor 48 is in this attitude, V belt 84 provides driving force to the high speed shaft 53 and at a speed related to that of the motor by the diameters of pulleys 85 and 86. Also when at this attitude, V belt 79 being slack, is essentially idle. Conversely, when V belt 79 is tightened by virtue of the motor 48 being in the attitude depicted in FIG. 6c, V belt 84 which is slack, is essentially idle.

Through the application of the procedure described in this invention, and with the further assistance of specialized equipment providing specific practical means for accomplishing it, facility is made available to:

Gauge the pre-existing in-situ stress that had been imposed upon a structural mass within its recollection span, by means of testing a sample extracted from that mass. By testing samples extracted from the same general location over the progress of time, it can be determined if the gauged stress is current or historic; and if current, estimate the rate of stress increase. Estimate the limiting continuous stress level on a structural mass, beyond which the structure could be reasonably expected to become hazardous within a practical future time frame. Characterize different materials by their individual patterns of acoustic emission response relative to the stress causing them.

Although preferred embodiments of the invention have been described herein in detail, it will be understood by those skilled in the art that variations may be made thereto without departing from the spirit of the invention or the scope of the appended claims.

I claim:

1. An apparatus for testing a prepared specimen comprising:
   at least a pair of platens each including a hard, flat and smooth loading face with at least one of the faces being perpendicular to a compressive axis of the apparatus and another of the faces being optionally free to rotationally adapt to a plane of a specimen end cap;
   means for applying gradually and substantially uniformly increasing compressive force on the specimen by moving in a relative manner the loading faces towards each other;
   means for measuring a compressive force applied by the loading faces to the specimen; and
   a single acoustic emission detecting device for mounting directly on an intermediate portion of a cylindrical face of the specimen, the detecting device including:
   an acoustic emission transducer for converting pulses emitted by such specimen under stress into detectable electronic signals;
   means for holding said detecting device in contact with such specimen;
   means for electronically filtering said electronic signals to pass only those signals in a frequency range typical of acoustic emission signals; and
   means for cumulatively counting a number of said signals passed by said filter means; and
   wherein an interface is defined between said detecting device and such specimen being tested, and further comprising a wave guide provided at a detecting end of said detecting device, said wave guide including:
   an end conforming to a cylindrical side wall shape of such specimen, and
   a couplant interposed between said wave guide and a detecting end of said detecting device and also between said wave guide and the specimen.

* * * * *